US010064944B2

(12) United States Patent
Wilson

(10) Patent No.: US 10,064,944 B2
(45) Date of Patent: Sep. 4, 2018

(54) LIQUID PHARMACEUTICAL COMPOSITION FOR THE TREATMENT OF A POSTERIOR EYE DISEASE

(71) Applicant: Clive G. Wilson, Glasgow (GB)

(72) Inventor: Clive G. Wilson, Glasgow (GB)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 14/973,461

(22) Filed: Dec. 17, 2015

(65) Prior Publication Data

US 2016/0101178 A1 Apr. 14, 2016

Related U.S. Application Data

(63) Continuation of application No. 13/884,785, filed as application No. PCT/EP2011/069795 on Nov. 10, 2011, now Pat. No. 9,241,900.

(30) Foreign Application Priority Data

Nov. 11, 2010 (EP) .................................. 10190832

(51) Int. Cl.
| | |
|---|---|
| A61K 47/06 | (2006.01) |
| A61K 47/34 | (2017.01) |
| A61K 31/405 | (2006.01) |
| A61K 31/573 | (2006.01) |
| A61K 31/7048 | (2006.01) |
| A61K 31/4168 | (2006.01) |
| A61K 31/57 | (2006.01) |
| A61K 9/00 | (2006.01) |
| A61K 9/08 | (2006.01) |

(52) U.S. Cl.
CPC ............ *A61K 47/06* (2013.01); *A61K 9/0048* (2013.01); *A61K 9/0051* (2013.01); *A61K 9/08* (2013.01); *A61K 31/405* (2013.01); *A61K 31/4168* (2013.01); *A61K 31/57* (2013.01); *A61K 31/573* (2013.01); *A61K 31/7048* (2013.01); *A61K 47/34* (2013.01)

(58) Field of Classification Search
CPC .... A61K 9/0048; A61K 47/06; A61K 9/0051; A61K 9/08; A61K 47/34; A61K 31/4168; A61K 31/57; A61K 31/573; A61K 31/7048; A61K 31/405
USPC .......................... 514/420, 401, 772, 743, 749
See application file for complete search history.

(56) References Cited

U.S. PATENT DOCUMENTS

| | | | |
|---|---|---|---|
| 10,022 A | 9/1853 | Stockwell | |
| 2,616,927 A | 11/1952 | Kauck et al. | |
| 5,077,036 A | 12/1991 | Long | |
| 5,326,566 A | 7/1994 | Parab | |
| 5,336,175 A | 8/1994 | Mames | |
| 5,518,731 A | 5/1996 | Meadows | |
| 5,667,809 A | 9/1997 | Trevino | |
| 5,874,469 A | 2/1999 | Maniar et al. | |
| 5,874,481 A | 2/1999 | Weers | |
| 5,980,936 A | 11/1999 | Krafft et al. | |
| 5,981,607 A | 11/1999 | Ding | |
| 6,042,845 A | 3/2000 | Sun et al. | |
| 6,113,919 A | 9/2000 | Cronelus | |
| 6,159,977 A | 12/2000 | Reeves | |
| 6,177,477 B1 | 1/2001 | George et al. | |
| 6,197,323 B1 | 3/2001 | Georgieff | |
| 6,224,887 B1 | 5/2001 | Samour et al. | |
| 6,262,126 B1 | 7/2001 | Meinert | |
| 6,294,563 B1* | 9/2001 | Garst .................... | A61K 31/557 514/392 |
| 6,372,243 B2 | 4/2002 | Kobuch et al. | |
| 6,391,879 B1 | 5/2002 | Reeves | |
| 6,458,376 B1 | 10/2002 | Meadows | |
| 6,486,212 B2 | 11/2002 | Meinert | |
| 6,489,367 B1 | 12/2002 | Meinert | |
| 6,730,328 B2 | 5/2004 | Maskiewicz | |
| 7,001,607 B1 | 2/2006 | Menz | |
| 7,026,359 B1 | 4/2006 | Gross | |
| 7,258,869 B1 | 8/2007 | Berry | |
| 7,740,875 B2 | 6/2010 | Dechow | |
| 8,029,977 B2 | 10/2011 | Meinert et al. | |
| 8,470,873 B2 | 6/2013 | Chen | |
| 8,614,178 B2 | 12/2013 | Theisinger et al. | |
| 8,796,340 B2 | 8/2014 | Theisinger et al. | |
| 8,986,738 B2 | 3/2015 | Meinert | |

(Continued)

FOREIGN PATENT DOCUMENTS

| | | |
|---|---|---|
| DE | 44 05 627 | 8/1995 |
| EP | 0 089 815 | 9/1983 |

(Continued)

OTHER PUBLICATIONS

Glossary of medical education terms, Institute of International Medical Education. http://www.iime.org/glossary.htm Accessed in Mar. 2013.*

Joussen et al. The concept of heavy tamponades—chances and limitations. Graefes Arch Clin Exp Ophthalmol (2008) 246:1217-1224.*

Blackie et al., "MGD: Getting to the Root Cause of Dry Eye", Review of Optometry, 2012, pp. 1-12.

Gerdenitsch, "Emulsions—established and promising drug carriers for parenteral administration", retrieved from internet: <http://ipimediaworld.com/wp-content/uploads/2012/05/Pages-from-IPI-Volume-2-Issue-1-11.pdf.> Retrieved on May 23, 2016.

(Continued)

*Primary Examiner* — Yih-Horng Shiao
(74) *Attorney, Agent, or Firm* — Hoxie & Associates LLC

(57) ABSTRACT

The invention provides pharmaceutical compositions based on liquid vehicles whose density is substantially higher than that of aqueous physiological fluids. The compositions are useful as medicines in ophthalmology, in particular for the treatment of conditions affecting the posterior segment of an eye. They may be administered topically into the eye or in a minimally invasive manner by periocular injection. Preferred liquid carriers are selected from semifluorinated alkanes.

17 Claims, No Drawings

(56) References Cited

U.S. PATENT DOCUMENTS

| | | |
|---|---|---|
| 9,241,900 B2 | 1/2016 | Wilson et al. |
| 9,308,262 B2 | 4/2016 | Gunther et al. |
| 9,770,508 B2 | 9/2017 | Günther et al. |
| 2002/0128527 A1 | 9/2002 | Meinert |
| 2003/0018044 A1 | 1/2003 | Peyman |
| 2003/0027833 A1 | 2/2003 | Cleary et al. |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson |
| 2005/0079210 A1 | 4/2005 | Gupta |
| 2005/0175541 A1 | 8/2005 | Lanza et al. |
| 2005/0288196 A1 | 12/2005 | Horn |
| 2006/1053905 | 7/2006 | Dario et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0260656 A1 | 10/2008 | Mallard |
| 2009/0149546 A1 | 6/2009 | Chang |
| 2010/0008996 A1 | 1/2010 | Meinert |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0159902 A1 | 6/2016 | Günther et al. |
| 2017/0087101 A1 | 3/2017 | Scherer et al. |
| 2017/0143832 A1 | 5/2017 | Günther et al. |

FOREIGN PATENT DOCUMENTS

| | | |
|---|---|---|
| EP | 0 670 159 | 9/1995 |
| EP | 0 965 329 | 12/1999 |
| EP | 0 965 334 | 12/1999 |
| EP | 1 152 749 | 11/2001 |
| EP | 0 939 655 | 6/2002 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| WO | WO 1995/033447 | 12/1995 |
| WO | WO 96/40052 | 12/1996 |
| WO | WO 1998/005301 | 12/1998 |
| WO | WO 00/10531 | 3/2000 |
| WO | WO 2000/024376 | 5/2000 |
| WO | WO 2000/054588 | 9/2000 |
| WO | WO 02/49631 A1 | 6/2002 |
| WO | WO 2005/018530 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 8/2007 |
| WO | WO 2008/060359 | 5/2008 |
| WO | WO 2009/013435 | 1/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 1/2013 |
| WO | WO 2013/110621 | 8/2013 |
| WO | WO 2014/041055 | 4/2014 |
| WO | WO 2014/041071 | 4/2014 |
| WO | WO 2014/154531 | 10/2014 |
| WO | WO 2015/011199 | 1/2015 |

OTHER PUBLICATIONS

Ishizaki et al., "Treatment of Diabetic Retinopathy", Forum: Complication, Practice, 2009, 26(5): 474-476 (3 pages).

Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.

Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.

Sato et al., "Vitrectomy and Intraocular Lens Implantation for Cytomegalovirus Retinitis in a Patient with Acquired Immunodeficiency Syndrome", Presented by Medical Online, New Ophthalmology, 1999, 16(7): 995-998 (4 pages).

Troiano et al., "Effect of Hypotonic .4% Hyaluronic Acid Drops in Dry Eye Patients: A Cross-Study", Cornea 27(10): 1126-1130 (Abstract Only), (2008).

"What is retinal vitrectomy?", Presented by: Medical Online, Obesity and Diabetes Mellitus, 2005, 4(2): 284-286 (3 pages).

Ahmed, et al., "Disposition of Timolol and Inulin in the Rabbit Eye Following Corneal Versus Non-Corneal Absorption," International Journal of Pharmaceutics, 1987, 38, 9-21.

Baerdemaeker, "Pharmacokinetics in Obese Patients," Continuing Education in Anaesthesia, Critical Care & Pain, 2004, 4, 152-155.

Broniatowski, et al., "Langmuir Monolayers Characteristice of Perfluorodecyl)-Alkanes," Journal of Physical Chemistry B, 2004, 108, 13403-13411.

Chemical Book, "5-Fluorouracil," available at http://www.chemicalbook.com/-ChemicalProductProperty_EN_CB8162744.htm>, accessed Mar. 7, 2014, 1 page.

Davies, "Biopharmaceutical Considerations in Topical Ocular Drug Delivery," Clinical and Experimental Pharmacology and Physiology, 2000, 27, 558-562.

Dembinski, et al., "Semi-fluorinated Alkanes as Carriers for Drug Targeting in Acute Respiratory Failure," Experimental Lung Research, 2010, 36, 499-507.

Elkeeb, et al., "Transungual Drug Delivery: Current Status," International Journal of Pharmaceutics, 2010, 384, 1-8.

English-language machine translation of EP0670159 (A1) issued in U.S. Appl. No. 14/122,025 on Apr. 1, 2015, 10 pages.

Freiburger Dokumentenserver (FreiDok), Albert-Ludwigs, Unversitat Feiburg im Breisgau, retrieved from the internet http://www.freidok.uni-freiburg.de/volltexte/5682/ , retrieved on Feb. 5, 2014, 2 pages.

(56) References Cited

OTHER PUBLICATIONS

Gayton, "Etiology, Prevalence, and Treatment of Dry Eye Disease," Clinical Ophthalmology, 2009, 3, 405-412.
Griffin, "Classification of Surface-Active Agents by 'HLB'," Journal of the Society of Cosmetic Chemists, 1949, 1, 311-326.
Hardung, "Semifluorierte und perfluorierte Vergindungen zur topischen und parenteralen Anwendung", 2008, retrieved from http://www.freidok.uni-freiburg.de/volltexte/5682/pdf/Dissertation_Hardung.pdf; Retrieved Oct. 10, 2011.
Hoerauf, et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.
International Preliminary Report on Patentability dated Apr. 23, 2013, for International Patent Application PCT/EP2011/068141, 4 Pages.
International Preliminary Report on Patentability dated May 14, 2013, for International Patent Application PCT/EP2011/069795, 8 Pages.
International Preliminary Report on Patentability dated Jul. 10, 2013, for International Patent Application PCT/EP2012/050043, 5 Pages.
International Preliminary Report on Patentability dated Nov. 26, 2013, for International Patent Application PCT/EP2012/059787, 9 Pages.
International Preliminary Report on Patentability dated Nov. 26, 2013, for International Patent Application PCT/EP2012/059788, 8 Pages.
International Preliminary Report on Patentability dated Jul. 29, 2014,for International Application No. PCT/EP2013/051163, 7 pages.
International Search Report for International Application No. PCT/EP2011/068141 dated Dec. 14, 2011, 2 pages.
International Search Report for International Patent Application PCT/EP2011/069795 dated Jan. 16, 2012, 3 pages.
International Search Report for International Patent Application PCT/EP2012/050043 dated Apr. 24, 2012, 2 pages.
International Search Report for International Application No. PCT/EP2012/059787 dated Dec. 5, 2012, 4 pages.
International Search Report for Intrenational Application No. PCT/EP2012/059788 dated Dec. 3, 2012, 4 pages.
International Search Report for Intrenational Application No. PCT/EP2013/051163 dated Mar. 4, 2013, 4 pages.
Knepp, et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.
Kociok, et al., "Influence on Membrane-Mediated Cell Activation by Vesicles of Silicone Oil or Perfluorohexyloctane," Graefe's Archive for Clinical and Experimental Ophthalmology, 2005, 243, 345-358.
Lemp, et al., "Management of Dry Eye Disease," The American Journal of Managed Care, 2008, 14 (3), S88-S101.
Mackiewicz, et al., "In Vivo Retinal Tolerance of Various Heavy Silicone Oils," Investigative Ophthalmology & Visual Science, 2007, 48 (4), 1873-1883.
Meinert, et al., "The Use of Semifluorinated Alkanes in Blood-Substitutes," Biomaterials, Artificial Cells, and Immobilization Biotechnology, 1993, 21 (5), 583-595.
Meinert, et al., "Semifluorinated Alkanes—A New Class of Compounds with Outstanding Properties for Use in Ophthalmology," European Journal of Ophthalmology, 2000, 10 (3), 189-197.
Murdan, et al., "Enhancing the Nail Permeability of Topically Applied Drugs," Expert Opinion on Drug Delivery, 2008, 5 (11), 1267-1282.
Perry, "Dry Eye Disease: Pathophysiology, Classification, and Diagnosis," The American Journal of Managed Care, 2008, 14 (3), S79-S87.
Pinarci, et al., "Intraocular Gas Application in the Diagnosis and Treatment of Valsalva Retiopathy in Case with Premacular Hemorrhage," XP002625604, Retina-Vitreus, 2009, 17 (2), 153-155, Abstract Only.
Plassmann, et al., "Trace Analytical Methods for Semifluorinated n-Alkanes in Snow, Soil, and Air," Analytical Chemistry, 2010, 82 (11), 4551-4557.
Plassmann, et al., "Theoretical and Experimental Simulation of the Fate of Semifluorinated n-Alkanes During Snowmelt," Environmental Science & Technology, 2010, 44(17), 6692-6697.
Rosca-Casian, et al., "Antifungal Activity of Aloe vera Leaves," Fitoterapia, 2007, 28, 219-222.
Rosenberg, "Effects of Protein Aggregates: An Immunologic Perspective," The AAPS Journal, 2006, 8 (3), E501-E507.
Stevenson, "Characterization of Protein and Peptide Stability and Solubility in Non-Aqueous Solvents," Current Pharmaceutical Biotechnology, 2000, 1, 165-182.
Wang, "Lyophilization and Development of Solid Protein Pharmaceuticals," International Journal of Pharmaceutics, 2000, 203, 1-60.
Wong, et al., "Perfluorocarbons and Semifluorinated Alkanes," Seminars in Ophthalmology, 2000, 15 (1), 25-35.
Bardin et al., "Long-Range Nanometer-Scale Organization of Semifluorinated Alkane Monolayers at the Air/Water Interface," Langmuir, 2011, 27:13497-13505.
Costa Gomes et al., "Solubility of dioxygen in seven fluorinated liquids," Journal of Fluorine Chemistry, 2004, 125, 1325-1329.
Dias et al., "Solubility of oxygen in liquid perfluorocarbons," Fluid Phase Equilibria, 2004, 222-223:325-330.
Gopal et al., "Use of intravitreal injection of triamcinolone acetonide in the treatment of age-related macular degeneration," Indian J Ophthalmol., 2007, 55(6):431-435.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability dated Sep. 18, 2012, for International Patent Application PCT/EP2011/053949, 9 Pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Preliminary Report on Patentability dated Jan. 26, 2016, for International Application No. PCT/EP2014/065840, 11 pages.
International Search Report for International Application No. PCT/EP2011/053949 dated Sep. 6, 2011, 5 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
Jonas et al., "Intravitreal triamcinolone acetonide for exudative age related macular degeneration," Br J Ophthalmol, 2003, 87:462-468.
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.
Mantle et al., "Adverse and beneficial effects of plant extracts on skin and skin disorders," Adverse Drug Reaction and Toxicological Reviews, 2001, 20(2): 89-103.
Schmutz et al., "Fluorinated Vesicles Made from Combinations of Phospholipids and Semifluorinated Alkanes. Direct Experimental

(56) References Cited

OTHER PUBLICATIONS

Evidence of the Location of the Semifluorinated Alkane within the Bilayer", Langmuir, 2003, 19:4889-4894.
Schnetler et al., "Lipid composition of human meibum: a review", S Afr Optom, 2013, 72(2), 86-93.
Spöler et al., "Towards a New in vitro Model of Dry Eye: The ex vivo Eye Irritation Test", Developments in Ophthalmology, 2010, 45, 93-107.
Tiffany, J.M., "Individual Variations in Human Meibomian Composition", Exp. Eye Res., 1978, 27, 289-300.
Wong et al., "Perfluorocarbons and Semifluorinated Alkanes," Seminars in Ophthalmology; vol. 15 (1), 2000, p. 25-35.
Xalatan, Latanoprost Ophthalmic Solution, 50 μg/mL Prostaglandin $F_{2\alpha}$ analogue, Product Monograph, Jul. 21, 2014, 30 pages.
Zhang et al., "Surface micelles of semifluorinated alkanes in Langmuir-Blodgett monolayers," Phys. Chem. Chem. Phys., 2004, 6:1566-1569.

\* cited by examiner

LIQUID PHARMACEUTICAL COMPOSITION FOR THE TREATMENT OF A POSTERIOR EYE DISEASE

CROSS REFERENCE TO RELATED APPLICATIONS

This application is a continuation of U.S. patent application Ser. No. 13/884,785, which is a National Stage Entry under 35 U.S.C. § 371 filed Jul. 29, 2013 of International Application No. PCT/EP2011/069795 filed Nov. 10, 2011, which claims the benefit of European Patent Application No. 10190832.5 filed Nov. 11, 2010, the contents of each of which are incorporated herein by reference.

BACKGROUND

The present invention relates to pharmaceutical compositions in liquid form which are suitable for the delivery of active ingredients to the posterior segment of an eye.

Today, ophthalmic diseases affecting tissues of the posterior segment of the eye are responsible for most cases of irreversible blindness worldwide. These include conditions such as glaucoma, age-related macular degeneration, diabetic retinopathy, and retinitis pigmentosa.

Glaucoma is a disease characterised by severe damage to the optic nerve leading to progressive, potentially irreversible loss of vision. The damage involves loss of retinal ganglion cells in a characteristic pattern. Glaucoma is often, but not always, associated with increased ocular pressure. According to WHO estimates, the disease contributed to more than 12% of all causes for blindness globally in 2002.

Age-related macular degeneration accounted for 8.7% of blindness worldwide in 2002. It is a condition involving damage to the retina in a pattern that leads to a loss of vision in the centre of the visual field, also known as the macula.

Diabetic retinopathy is an ocular condition which affects up to 80% of all patients who have had diabetes for 10 years or more, and accounts for about 5% of the incidence of blindness worldwide. The retinopathy is the result of microvascular retinal changes. A hyperglycaemia-induced death of ocular pericytes leads to capillary wall damage and potentially oedema, such as macular oedema. In the absence of treatment, blurred vision and eventually blindness may develop as a result.

Retinitis pigmentosa describes a group of ophthalmic diseases which have a genetic origin, and which are characterised by progressive retinal dystrophy, i. e. a degeneration of the photoreceptors or the retinal pigment epithelium resulting in a loss of vision. The condition often becomes manifest in the form of impaired dark adaptation or nyctalopia, often followed by reduction of the peripheral visual field. At a progressed stage of the disease, it may involve the loss of central vision.

For at least some of the diseases affecting the tissues of the posterior segment of the eye, it may be possible to slow their progression, reduce the severity of symptoms, or even substantially control the condition by pharmacotherapy. For example, in the case of glaucoma, several classes of active agents have been used with significant success, including prostaglandin analogs (such as latanoprost, bimatoprost, and travoprost), beta-adrenergic receptor antagonists (such as timolol, levobunolol, and betaxolol), alpha-2-adrenergic agonists (such as brimonidine), and carbonic anhydrase inhibitors (such as dorzolamide, brinzolamide, and acetazolamide).

The effective delivery of active agent to the posterior eye, however, remains to be a major problem in ophthalmology. Most commonly, ophthalmic pharmacotherapy relies on the topical administration of—typically liquid—formulations to the front of the eye. Most patients are well familiar with eye droppers, their use is perceived as relatively simple and convenient, and the non-invasive nature of the topical route makes it predestined for self-administration.

On the other hand, only a small fraction of a topically administered drug substance—typically less than about 5%—reaches the location where its pharmacological activity is required. Only a fraction of the volume of a formulation which is administered (which is usually about 30 to 50 µl) due to the limited volume capacity of the lacrimal sac: a significant fraction of the administered fluid volume is expelled by the blinking of the eyelids, and another fraction is taken up systemically via the nasolacrimal duct, which potentially leads to adverse drug effects. The fraction of the drug substance which does reach the posterior segment of the eye after topical administration into the fornix of the conjunctiva must first diffuse through the lacrimal film, the cornea (which represents a major barrier for most drugs), the anterior aqueous chamber, and the vitreous chamber, which diffusion path is characterised by a relatively small area, a relatively long diffusion distance, and several competing pathways which lead to drug loss. Depending on the nature of a drug substance, it may therefore be rather challenging to obtain therapeutic concentrations in the posterior segment of the eye.

In recent years, a number of alternatives to the topical route of ophthalmic delivery have been investigated. In particular, new methods, devices and compositions for intraocular and periocular administration have been proposed.

Intravitreal injections are the most direct approach to drug delivery to the posterior segment, and it is much more likely to obtain and maintain therapeutic drug levels following such type of injection than after topical delivery. A drawback of this route is that the vitreous liquid undergoes some relatively rapid turnover, so that drugs introduced into it are quickly eliminated. At the same time, intravitreal injections require the service of a specialised physician; they are clearly unfeasible for self-administration or for administration by a nurse. For patients, the mode of injection is highly uncomfortable and may be substantially painful in spite of local anaesthesia. Since many of the conditions affecting the posterior eye are of chronic or sub-chronic nature, intravitreal injection would have to be performed on a regular basis, which is even less acceptable to patients and brings about some considerable risk of iatrogenic eye infections and damage to the eye.

In order to somewhat improve patient convenience, depot formulations for intravitreal administration have been developed. These are still injected into the eye ball, or perhaps even require more extensive ophthalmic surgery to insert (and to remove, depending on the particular delivery system), but the frequency of administration can be substantially reduced. Among the proposed formulation designs are colloidal drug carriers such as liposomes, dendrimers, polymeric microparticles, and gels, but also solid implants, such as disclosed in WO 2010/062394 and WO 2008/060359. These delivery systems may provide for drug release over periods of several days, weeks, or months, depending on the nature of the drug carrier.

To avoid the inconvenience and risks associated with intravitreal injections, various forms of periocular administration have been developed as alternatives. These include in particular sub-Tenon's, subconjunctival or retrobulbar injections. This approach to drug delivery is considered safer and somewhat less invasive than intravitreal injection and also offers some potential for localised drug depots. The sub-Tenon's injection technique typically uses a short needle introduced through the superotemporal bulbar conjunctiva into the sub-Tenon's space while the patient is instructed to look inferonasally. The cannula is then advanced posteriorly along the globe in a gently sweeping motion to prevent accidental eyeball penetration until the hub reaches the conjunctival entry site, when the formulation is discharged. In a typical subconjunctival injection procedure, a needle is inserted and the medication delivered into the space between the conjunctiva and the sclera. Retrobulbar injections are frequently administered for providing local anaesthesia. A medium-short needle is inserted at the inferolateral border of the bony orbit and advanced straight back for about 1.5 cm until it has passed the equator of the globe. Then it is directed medially and upwards toward the apex of the orbit, penetrating the muscle cone delineating the retrobulbar space. Several milliliters of injection volume can be delivered to this site.

However, it is obvious that also these injection techniques, even though perhaps somewhat less distressing than intravitreal injections, are not at all convenient to patients or free of risk with respect to inadvertent bulb penetration or infection.

Thus there remains a clear need for improved delivery methods for drugs which act in the posterior segment of the eye. More specifically, there is a need for methods having a potential to achieve are more target-specific, effective delivery of therapeutic compounds to the tissues of the posterior eye. In particular, there is a need for methods which overcome one or more of the disadvantages of the currently known ophthalmic drug delivery methods. Moreover, methods are needed which are safer and more convenient than the currently practised methods. In a further aspect, there is a need for pharmaceutical compositions and kits which are useful for practising such improved methods.

It is therefore an object of the present invention to provide such improved delivery methods for active ingredients acting in the posterior eye. A further object is to provide methods which overcome one or more disadvantages that are associated with the commonly known and practised delivery methods. In a further aspect, it is an objective of the invention to provide pharmaceutical compositions which are suitable for carrying out such methods. These and further objects will become clear on the basis of the description of the invention and the patent claims.

SUMMARY OF THE INVENTION

In a first aspect, the present invention provides a method for treating a disease or condition of a tissue associated with the posterior segment of an eye of a patient. The method comprises a first step of administering a pharmaceutical composition comprising a non-aqueous, physiologically tolerable, liquid vehicle having a density of at least 1.2 g/ml, either by topical administration to the surface of the eye and/or by periocular injection, followed by a second step of bringing the patient into a supine position facing upwards for a sufficiently long time period to allow the composition to migrate from the site of administration to a site in the posterior segment of the eye.

In a further aspect, the invention provides a pharmaceutical composition for the treatment of a tissue associated with the posterior segment of an eye of a patient. The composition comprises a non-aqueous, physiologically tolerable, liquid vehicle having a density of at least 1.2 g/ml, and it is administered by topical administration to the surface of the eye and/or periocular injection. Preferably, the treatment includes a time period subsequent to the administration of the composition during which period the patient is in a supine position facing upwards, wherein said period is sufficiently long to allow the composition to migrate from the site of administration to a site in the posterior segment of the eye.

Preferably, the dense, non-aqueous liquid vehicle comprises a perfluorocarbon, semifluorinated alkane, and/or polysiloxane. In particular, semifluorinated alkanes are highly useful for carrying out the invention.

The method and composition of the invention may be used to provide for sustained release of an incorporated active ingredient to the posterior segment of an eye, and are beneficial in the management of various eye diseases such as age-related macular degeneration, diabetic retinopathy, glaucoma, retinitis pigmentosa, and cytomegalovirus retinitis.

DETAILED DESCRIPTION OF THE INVENTION

The present invention provides a method for treating a disease or condition of a tissue associated with the posterior segment of an eye of a patient. The method comprises a first step of administering a pharmaceutical composition comprising a non-aqueous, physiologically tolerable, liquid vehicle having a density of at least about 1.2 g/ml, either by topical administration to the surface of the eye and/or by periocular injection. Following the administration of the composition, the patient is brought into a supine position facing upwards for a sufficiently long time period to allow the composition to migrate from the site of administration to a site in the posterior segment of the eye.

Moreover, the invention provides a pharmaceutical composition for the treatment of a tissue associated with the posterior segment of an eye of a patient. The composition comprises a non-aqueous, physiologically tolerable, liquid vehicle having a density of at least 1.2 g/ml, and it is administered by topical administration to the surface of the eye and/or periocular injection. Preferably, the treatment includes a time period subsequent to the administration of the composition during which period the patient is in a supine position facing upwards, wherein said period is sufficiently long to allow the composition to migrate from the site of administration to a site in the posterior segment of the eye.

As used herein, the posterior segment of the eye comprises any ophthalmic tissue or structure posterior to (and including) the anterior hyaloid membrane, such as the vitreous humor, the retina, the choroid, the sclera, the retinal blood vessels, the optic disk, the hyaloid canal, and the optic nerve.

A pharmaceutical composition is a composition of typically at least one active pharmaceutical compound and one or more excipients which is useful in the prevention, diagnosis, stabilisation, treatment, or—generally speaking—management of a condition or disease. As used herein, treatment refers to any type of pharmaceutical use of such composition, including any prophylactic or preventive use, and in particular any use for stabilising, managing, or curing a disease or pathological condition, or the improvement of symptoms associated therewith.

A liquid vehicle is understood as a liquid excipient or mixture of excipients serving as a carrier for an active ingredient and enabling its proper administration. A liquid vehicle is liquid at normal temperature, but of course may be solid at lower temperatures. Non-aqueous refers to the property of being substantially free of water. However, this does not exclude the presence of residual amounts of water as commonly contained in non-aqueous organic liquids. Physiologically tolerable means that a vehicle or excipient is acceptable for pharmaceutical use in consideration of the intended route of administration, frequency of use, severity of the condition that is treated, and amount of vehicle administered per dosing.

An important feature of the invention is the high density of the non-aqueous vehicle comprised in the pharmaceutical composition. In essence, the density of the vehicle is selected to be substantially higher than that of physiological fluids, including the lacrimal fluid as well as the interstitial fluid, which are both rather similar to water or slightly denser than water. In contrast, the density of the non-aqueous vehicle according to the invention is much higher, preferably at least about 1.2 g/cm$^3$. In a further embodiment, the density of the vehicle is at least about 1.25 g/cm$^3$, 1.3 g/cm$^3$, or 1.35 g/cm$^3$, respectively. Moreover, it is preferred that the density of the pharmaceutical composition as a whole is, by virtue of its content of the dense non-aqueous vehicle, also substantially higher than that of water, such as at least about 1.2 g/cm$^3$, 1.25 g/cm$^3$, in particular at least about 1.3 g/cm$^3$.

Topical administration to the surface of an eye means non-invasive administration of a pharmaceutical composition into the inferior fornix of the conjunctiva of an eye, or onto any external structure of the front of an eye, such as onto the cornea. In one of the preferred embodiments, the composition of the invention is indeed topically administered. Alternatively or additionally, the composition may be administered by periocular injection. Such periocular injection may be carried out as sub-Tenon's or subconjunctival injections, as described herein-above.

After receiving the composition, the patient is placed in a supine position, or instructed to bring himself into a supine position, holding the face upwards. It may not he necessary that the whole body of the patient is supine as long as the head is in the required position. Unexpectedly, the inventors have found that—probably by virtue of the high density of the non-aqueous vehicle, even though they do not wish to be bound by this theory—the supine position of the head effects a migration of the topically or periocularly administered composition towards the retrobulbar region where it forms a depot from which an active ingredient incorporated within the composition is release gradually over time. The effect is most pronounced if the vehicle is selected to be substantially water-immiscible. The supine position must be maintained for a sufficiently long period of time to allow the composition, or at least a pharmacologically relevant fraction thereof, to migrate from the site of administration to the site in the posterior segment of the eye. The exact duration required for this to happen depends, inter alfa, on the precise mode of administration, the actual density of the composition, and its volume. In one of the preferred embodiments, the supine position is maintained over at least about 15 minutes. In another embodiment, it is maintained over at least about 30 minutes, or at least about 1 hour, or at least about 2 hours, 3 hours, 4 hours, or 6 hours, respectively.

As mentioned, a key feature of the invention is that the non-aqueous vehicle used in the composition has a particularly high density, and in a preferred embodiment, the density of the whole composition is also particularly high, i.e. substantially higher than that of the aqueous fluids of the body. It is also preferred that the dense non-aqueous vehicle makes up most of the liquid phase of the composition, such as at least about 60 wt.-%, and more preferably at least about 80 wt.-%, or at least about 90 wt.-%, or at least about 95 wt.-%. In a particularly useful embodiment, the liquid phase of the composition consists of the non-aqueous vehicle having a density as described above, which however would not exclude the presence of some residual amounts of other liquids having little or no technical impact.

Potentially useful liquid vehicles may be selected, for example, from perfluorocarbons, semifluorinated alkanes, polysiloxanes, and mixtures thereof. In one of the preferred embodiments, the vehicle is a semifluorinated alkane or mixture of semifluorinated alkanes. Semifluorinated alkanes are linear or branched alkanes some of whose hydrogen atoms have been replaced by fluorine. In a preferred embodiment, the semifluorinated alkanes (SFA's) used in the present invention are composed of at least one non-fluorinated hydrocarbon segment and at least one perfluorinated hydrocarbon segment. Particularly useful are SFA's which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFA's having two or three segments as RFRH and RFRHRF, respectively, wherein RF designates a perfluorated hydrocarbon segment, RH designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFA's which are useful in the context of the present invention are also described in EP-A 965 334, EP-A 965329 and EP-A 2110126, the disclosure of which documents is incorporated herein.

In a further embodiment, the semifluorinated alkane is a compound according to the formula RFRH, whose segments $R_F$ and $R_H$ are linear and each—but independently from one another—have from 3 to 20 carbon atoms. In another particular embodiment, the perfluorinated segment is linear and comprises from 4 to 12 carbon atoms, and/or the non-fluorinated segment is linear and comprises from 4 to 8 carbon atoms. Preferred SFA's include in particular the compounds F4H5, F4H6, F6H4, F6H6, F6H8, and F6H10. Presently most preferred for carrying out the invention are F4H5, F6H6 and F6H8.

Optionally, the composition may comprise more than one SFA. It may be useful to combine SFA's, for example, in order to achieve a particular target property such as a certain density or viscosity. If a mixture of SFA's is used, it is furthermore preferred that the mixture comprises at least one of F4H5, F4H6, F6H4, F6H6, F6H8, and F6H10, and in particular one of F4H5, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFA's are chemically and physiologically inert, colourless and stable. Their typical densities range from 1.1 to 1.7 g/cm$^3$, and their surface tension may be as low as 19 mN/m. SFA's of the RFRH type are insoluble in water but also somewhat amphiphilic, with increasing lipophilicity correlating with an increasing size of the non-fluorinated segment. Again, for practising the current invention, an SFA having a density of at least 1.2 g/cm$^3$ should be selected.

Liquid SFA's of the RFRH type are being used commercially for unfolding and reapplying a retina, for long-term tamponade as vitreous humor substitute (H.

Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds. On the other hand, SFA's have not been used as excipients in approved drug products as of today.

It has now surprisingly been found by the inventors that SFA's having the specified density are particularly suitable as carriers, vehicles or excipients in ophthalmic compositions for topical or minimally invasive administration. This is not only based on the observation that the respective compositions are capable of migrating towards the posterior segment of the eye after administration, but also on the fact that SFA's are capable of dissolving many poorly water-soluble compounds which are of interest in ophthalmology. Moreover, they are unexpectedly well-tolerated by the eye, as shown in preclinical testing. This is very surprising as many organic or non-aqueous solvents, perhaps with the exception of oily compounds and the vehicles specified in the context of the invention, are typically very irritating or even highly damaging when administered topically to an eye.

Compared to oily carriers or vehicles in ophthalmic compositions for topical use, SFA's exhibit a refractive index which is much better compatible with the aim of a minimally affected vision: While oily preparation lead to a blurry vision and can therefore not be administered in any situation in which the patient needs a clear vision, SFA's cause little or no blurring.

By illustration, the refractive index of tear fluid is close to that of water, i.e. 1.333 at room temperature (RT). Oils typically have a substantially higher refractive index such as about 1.46 (peanut oil), 1.47 (sesame oil), or 1.48 (castor oil). In contrast, the inventors have determined the refractive indices of various SFA's of interest to be in the region of 1.29 to 1.35, i.e. much closer to that of water. In one of the specific embodiments, the invention is therefore practised with an SFA whose refractive index is from 1.29 to 1.35, and in particular from about 1.30 to about 1.35 at 20° C. The refractive index for selected SFA's is shown in table 1.

Moreover, SFA's exhibit a remarkable wetting and spreading behaviour by which they deliver an incorporated active ingredient rapidly and effectively to the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each other.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

TABLE 1

| SFA | Refractive index |
| --- | --- |
| F4H4 | 1.308 |
| F4H5 | 1.3204 |
| F4H6 | 1.334 |
| F4H7 | 1.3357 |
| F4H8 | 1.348 |
| F6H2 | 1.295 |
| F6H4 | 1.306 |
| F6H6 | 1.3224 |
| F6H7 | 1.3366 |
| F6H8 | 1.3432 |
| F6H9 | 1.3494 |

A low contact angle of less than 90° indicates high wettability and/or spreading, whereas a higher contact angle indicates poor wettability and spreading. Perfect wetting and spreading results in a contact angle of 0°, also reported as no measurable contact angle.

The inventors have found that the SFA's used in the present invention, in particular the preferred SFA's, exhibit an excellent wetting of various surfaces which are not easily wetted by conventional drug formulations. For example, the contact angle of both F4H5 and F6H8 on tablets compressed from either trospium chloride or fenofibrate (150 mg of drug substance compressed at 15-20 kN to tablets of 13 mm in diameter) was not measurable, i.e. perfect wetting occurred. It is noted that fenofibrate is an example of a hydrophobic, poorly water-soluble compound, whereas trospium chloride is hydrophilic and water-soluble. In comparison, the contact angle of purified water on the fenofibrate tablet was determined as 92.5°, i.e. the tablet was poorly wetted by water.

A further surprising advantage of SFA's found by the inventors is that they appear to form very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct. Hence, if an effective dose of an active ingredient can be incorporated in a small volume of liquid which can be dispensed as a very small droplet, this should lead to a substantially increased dosing reliability and reproducibility, thus enhancing the safety and effectiveness of the therapy.

Moreover, the invention provides a means of formulating non-aqueous ophthalmic compositions which are microbiologically stable. This is due to the fact that SFA's are not normally prone to microbial contamination. Hence, it is possible to formulate preservative-free ophthalmic compositions which are better tolerable for many patients, in particular patients suffering from an ophthalmic disease.

In a further preferred embodiment, the non-aqueous vehicle having a density of at least about 1.2 g/cm$^3$ is selected to have a boiling point of at least about 120° C. In the context of the present invention, it is advantageous in particular in the case of topical administration that the vehicle does not evaporate rapidly, but remains available for migrating towards the site of drug action and/or forming a drug depot at a site associated with the posterior segment of the eye. In another embodiment, the boiling point is at least about 125° C.

According to a particular embodiment, the vehicle is also selected to exhibit a dynamic viscosity of not more than about 5 mPas, or not more than about 3.5 mPas, respectively. Depending on the exact formulation and mode of administration, it may be advantageous to use a low viscosity vehicle in order to achieve a sufficiently high rate of flux of the formulation from the site of administration to the posterior segment of the eye.

The composition of the invention may further comprise one or more additional excipients (other than the non-aqueous vehicle or vehicles). Such excipients may be selected from commonly known pharmaceutical ingredients which are physiologically tolerable and suitable for ophthalmic and/or parenteral use, depending on the intended mode of administration, such as from suitable cosolvents, surfactants, stabilisers, antioxidants, preservatives, colouring agents, and the like.

If a cosolvent is required, it should preferably be incorporated in a small amount. Potentially suitable organic cosolvents may be selected from glyceride oils, liquid waxes, and liquid paraffin, or an organic solvent exhibiting a high degree of biocompatibility. Examples of potentially useful oily excipients which may be used in combination with one or more SFA's include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye. In one of the preferred embodiments, the concentration of the oily excipient is up to about 30 wt.-%, such as in the range from about 0.1 to 20 wt.-%.

Examples of potentially useful organic solvents include glycerol, propylene glycol, polyethylene glycol, and ethanol. However, the concentration of the cosolvent should preferably be low relative to that of the SFA or SFA mixture. If an organic solvent such as ethanol is used, it is recommendable to keep it below a level of approx 5 wt.-%. More preferably, the content of ethanol is from about 0.1 to about 2 wt.-%, and most preferably not more than about 1 wt.-%.

Surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, and mixtures of two or more thereof.

Furthermore, the invention provides a pharmaceutical kit comprising the composition as described above and a container holding the composition. Preferably, the container which contains the composition has a dispensing means such as a dropping device adapted for topically administering the composition to the eye of a patient.

As already mentioned, the method, the composition and/or the kit according to the present invention may be used in the treatment of a disease or condition affecting a tissue associated with the posterior segment of an eye of a patient. Examples of such diseases are age-related macular degeneration, diabetic retinopathy, glaucoma, retinitis pigmentosa, and cytomegalovirus retinitis, to mention only a few.

Depending on the disease which is to be treated, one or more suitable active ingredients may be incorporated, e.g. in dissolved or dispersed form. As used herein, the dispersed form refers to a composition comprising at least two phases, i.e. a continuous or coherent phase (which is liquid in the case of the composition of the invention) and at least one dispersed (or internal, or incoherent) phase, which may be liquid if the system is an emulsion, or solid in the case of a suspension.

Suitable active ingredients include, e. g.,
  prostaglandin analogues useful in the management of increased intraocular pressure, such as latanoprost, bimatoprost, tafluprost, travoprost and unoprostone;
  corticosteroids useful in the management of inflammatory processes, such as triamcinolone, dexamethasone, fluorometholone, hydrocortisone, prednisolone, and rimexolone;
  antibiotics, such as aureomycin, azithromycin, gentamycin, ciprofloxacin, ofloxacin, fusidic acid, kanamycin, levofloxacin, lomefloxacin, oxyteiracyclin, tobramycin, natamycin, gentamycin, and moxifloxacin;
  beta-adrenergic antagonists useful for reducing the intraocular pressure, such as carteolol, timolol, metipranolol, betaxolol, pindolol, and levobunolol;
  cholinergic agents useful in the management of glaucoma, such as brimonidine, clonidine, dipivefrine, apraclonidine, carbachol, and pilocarpine;
  carbonic anhydrase inhibitors useful in the management of glaucoma, such as brinzolamide and dorzolamide;
  virustatic agents useful for ophthalmic administration, such as aciclovir, trifluridine, and ganciclovir; and
  nonsteroidal anti-inflammatory drugs, such as diclofenac, bromfenac, ketorolac, flurbiprofen, and indometacin, including any salts and solvates thereof.

The invention claimed is:

1. A method for the stabilization, management or cure, or improvement of the symptoms, of a disease or condition affecting a tissue of the posterior segment of an eye of a patient, comprising topical administration to the surface of the eye of a pharmaceutical composition comprising an active ingredient dissolved in a non-aqueous, physiologically tolerable, liquid vehicle having a density of at least 1.2 g/ml wherein the liquid vehicle comprises a semifluorinated alkane, wherein the semifluorinated alkane has a refractive index in the range from 1.3204 to 1.3494.

2. The method of claim 1, wherein the method further includes a time period subsequent to the administration of the composition during said period the patient is in a supine position facing upwards, said period being from about 15 minutes to about 6 hours to allow the composition to migrate from the site of administration to a site in the posterior segment of the eye.

3. The method of claim 1, wherein the patient is affected by a disease or condition selected from the group consisting of age-related macular degeneration, diabetic retinopathy, glaucoma, retinitis pigmentosa, and cytomegalovirus retinitis.

4. The method of claim 1, wherein the liquid vehicle further comprises one or more compounds selected from the group consisting of perfluorocarbons, polysiloxanes, and mixtures thereof.

5. The method of claim 1, wherein the semifluorinated alkane is a compound of the formula

RFRH or of formula

RFRHRF wherein RF is a perfluorinated hydrocarbon segment with 20 or less carbon atoms, and wherein RH is a non-fluorinated hydrocarbon segment with 3 to 20 carbon atoms.

6. The method of claim 5, wherein the semifluorinated alkane is a compound of formula

RFRH wherein RF is a linear perfluorinated hydrocarbon segment with 3 to 10 carbon atoms, and wherein RH is a linear alkyl group with 3 to 10 carbon atoms.

7. The method of claim 6, wherein the semifluorinated alkane is selected from the group consisting of F4H5, F6H6 and F6H8.

8. The method of claim 1, wherein the liquid vehicle has a density of at least about 1.35 g/ml.

9. The method of claim 1, wherein the liquid vehicle has a boiling point of at least about 120° C.

10. The method of claim 1, wherein the pharmaceutical composition has a dynamic viscosity of not more than about 5 mPas.

11. The method of claim 1, wherein the semifluorinated alkane has a refractive index of 1.3432 at 20° C.

12. The method of claim 1, wherein the pharmaceutical composition consists of the active ingredient dissolved in the semifluorinated alkane.

13. The method of claim 1, wherein the pharmaceutical composition further comprises one or more excipients selected from the group consisting of co-solvents, surfactants, stabilisers, antioxidants, preservatives, and colouring agents.

14. The method of claim 1, wherein the pharmaceutical composition is formulated so as to provide for the sustained release of the active ingredient over a period of at least about 24 hours.

15. The method of claim 1, wherein the pharmaceutical composition comprises the active ingredient in dissolved form, wherein the active ingredient is a cholinergic agent selected from the group consisting of brimonidine, clonidine, dipivefrine, apraclonidine, carbachol, and pilocarpine, and salts or solvates thereof.

16. The method of claim 15, wherein the active ingredient is brimonidine or a salt or solvate thereof.

17. The method of claim 12, wherein the active ingredient is selected from the group consisting of latanoprost, bimatoprost, tafluprost, travoprost, unoprostone, triamcinolone, dexamethasone, fluorometholone, hydrocortisone, prednisolone, rimexolone, aureomycin, azithromycin, gentamycin, ciprofloxacin, ofloxacin, fusidic acid, kanamycin, levofloxacin, lomefloxacin, oxytetracyclin, tobramycin, natamycin, moxifloxacin, carteolol, timolol, metipranolol, betaxolol, pindolol, levobunolol, brimonidine, clonidine, dipivefrine, apraclonidine, carbachol, pilocarpine, brinzolamide, dorzolamide, aciclovir, trifluridine, ganciclovir, diclofenac, bromfenac, ketorolac, flurbiprofen, indomethacin, and salts and solvates thereof.

* * * * *